United States Patent
Hossainy et al.

(10) Patent No.: US 7,875,283 B2
(45) Date of Patent: Jan. 25, 2011

(54) BIODEGRADABLE POLYMERS FOR USE WITH IMPLANTABLE MEDICAL DEVICES

(75) Inventors: Syed F. A. Hossainy, Fremont, CA (US); Debashis Dutta, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1351 days.

(21) Appl. No.: 11/155,036

(22) Filed: Jun. 16, 2005

(65) Prior Publication Data

US 2005/0232971 A1 Oct. 20, 2005

Related U.S. Application Data

(63) Continuation-in-part of application No. 10/104,772, filed on Mar. 20, 2002, now abandoned, which is a continuation-in-part of application No. 09/548,533, filed on Apr. 13, 2000, now Pat. No. 6,527,801.

(51) Int. Cl.
A61F 2/00 (2006.01)
(52) U.S. Cl. .................................................. 424/423
(58) Field of Classification Search ................ 623/1.11, 623/1.18, 1.19, 1.38, 1.4–1.472; 427/2.24, 427/2.14, 2.25, 2.26; 424/422, 423, 424, 424/426, 484
See application file for complete search history.

(56) References Cited

U.S. PATENT DOCUMENTS

| | | | |
|---|---|---|---|
| 3,839,743 A | 10/1974 | Schwarcz | |
| 3,900,632 A | 8/1975 | Robinson | |
| 4,110,497 A | 8/1978 | Hoel | |
| 4,321,711 A | 3/1982 | Mano | |
| 4,346,028 A | 8/1982 | Griffith | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,768,507 A | 9/1988 | Fischell et al. | |
| 4,776,337 A | 10/1988 | Palmaz | |
| 4,816,339 A | 3/1989 | Tu et al. | |
| 4,850,999 A | 7/1989 | Planck | |
| 4,877,030 A | 10/1989 | Beck et al. | |
| 4,878,906 A | 11/1989 | Lindemann et al. | |
| 4,879,135 A | 11/1989 | Greco et al. | |
| 4,902,289 A | 2/1990 | Yannas | |
| 4,977,901 A | 12/1990 | Ofstead | |
| 4,994,298 A | 2/1991 | Yasuda | |
| 5,019,090 A | 5/1991 | Pinchuk | |
| 5,028,597 A | 7/1991 | Kodama et al. | |
| 5,059,211 A | 10/1991 | Stack et al. | |
| 5,062,829 A | 11/1991 | Pryor et al. | |
| 5,084,065 A | 1/1992 | Weldon et al. | |
| 5,085,629 A | 2/1992 | Goldberg et al. | |
| 5,100,429 A | 3/1992 | Sinofsky et al. | |
| 5,108,755 A | 4/1992 | Daniels et al. | |
| 5,112,457 A | 5/1992 | Marchant | |
| 5,123,917 A | 6/1992 | Lee | |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,167,614 A | 12/1992 | Tessmann et al. | |
| 5,192,311 A | 3/1993 | King et al. | |
| 5,197,977 A | 3/1993 | Hoffman, Jr. et al. | |
| 5,234,456 A | 8/1993 | Silvestrini | |
| 5,234,457 A | 8/1993 | Andersen | |
| 5,236,447 A | 8/1993 | Kubo et al. | |
| 5,279,594 A | 1/1994 | Jackson | |
| 5,282,860 A | 2/1994 | Matsuno et al. | |
| 5,289,831 A | 3/1994 | Bosley | |
| 5,290,271 A | 3/1994 | Jernberg | |
| 5,306,286 A | 4/1994 | Stack et al. | |
| 5,306,294 A | 4/1994 | Winston et al. | |
| 5,328,471 A | 7/1994 | Slepian | |
| 5,330,500 A | 7/1994 | Song | |
| 5,342,348 A | 8/1994 | Kaplan | |
| 5,342,395 A | 8/1994 | Jarrett et al. | |
| 5,342,621 A | 8/1994 | Eury | |
| 5,356,433 A | 10/1994 | Rowland et al. | |
| 5,383,925 A | 1/1995 | Schmitt | |
| 5,385,580 A | 1/1995 | Schmitt | |
| 5,389,106 A | 2/1995 | Tower | |
| 5,441,515 A | 8/1995 | Khosravi et al. | |
| 5,443,458 A | 8/1995 | Eury | |
| 5,455,040 A | 10/1995 | Marchant | |
| 5,464,650 A | 11/1995 | Berg et al. | |
| 5,502,158 A | 3/1996 | Sinclair et al. | |
| 5,514,379 A | 5/1996 | Weissleder et al. | |
| 5,527,337 A | 6/1996 | Stack et al. | |
| 5,554,120 A | 9/1996 | Chen et al. | |
| 5,578,073 A | 11/1996 | Haimovich et al. | |

(Continued)

FOREIGN PATENT DOCUMENTS

DE 44 07 079 9/1994

(Continued)

OTHER PUBLICATIONS

Notification of Refusal issued by JPO on Oct. 13, 2009, in connection with Appl. No. 2003-577971, 3 pgs.

(Continued)

Primary Examiner—Kevin T Truong
(74) Attorney, Agent, or Firm—Squire, Sanders & Dempsey L.L.P.

(57) ABSTRACT

The present invention relates to a stent fabricated of or coated with a composition comprising a biodegradable hydrophobic polymer containing water-labile bonds such that a device fabricated of the composition or the surface of a device coated with the requisite mechanical characteristics required of a stent and the polymer erodes from its outer surface inward.

20 Claims, No Drawings

U.S. PATENT DOCUMENTS

| | | | |
|---|---|---|---|
| 5,591,607 A | 1/1997 | Gryaznov et al. |
| 5,593,403 A | 1/1997 | Buscemi |
| 5,599,301 A | 2/1997 | Jacobs et al. |
| 5,599,922 A | 2/1997 | Gryaznov et al. |
| 5,605,696 A | 2/1997 | Eury et al. |
| 5,629,077 A | 5/1997 | Turnlund et al. |
| 5,631,135 A | 5/1997 | Gryaznov et al. |
| 5,637,113 A | 6/1997 | Tartaglia et al. |
| 5,667,767 A | 9/1997 | Greff et al. |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,716,981 A | 2/1998 | Hunter et al. |
| 5,726,297 A | 3/1998 | Gryaznov et al. |
| 5,728,751 A | 3/1998 | Patnaik |
| 5,733,925 A | 3/1998 | Kunz et al. |
| 5,741,881 A | 4/1998 | Patnaik |
| 5,756,476 A | 5/1998 | Epstein et al. |
| 5,756,477 A | 5/1998 | Wang et al. |
| 5,766,710 A | 6/1998 | Turnlund et al. |
| 5,800,516 A | 9/1998 | Fine et al. |
| 5,811,447 A | 9/1998 | Kunz et al. |
| 4,739,762 A | 10/1998 | Palmaz |
| 5,824,048 A * | 10/1998 | Tuch ........................ 623/1.42 |
| 5,824,049 A | 10/1998 | Ragheb et al. |
| 5,830,178 A | 11/1998 | Jones et al. |
| 5,830,461 A | 11/1998 | Billiar et al. |
| 5,830,879 A | 11/1998 | Isner |
| 5,833,651 A | 11/1998 | Donovan et al. |
| 5,834,582 A | 11/1998 | Sinclair et al. |
| 5,837,313 A | 11/1998 | Ding et al. |
| 5,837,835 A | 11/1998 | Gryaznov et al. |
| 5,851,508 A | 12/1998 | Greff et al. |
| 5,854,207 A | 12/1998 | Lee et al. |
| 5,855,618 A | 1/1999 | Patnaik et al. |
| 5,858,746 A | 1/1999 | Hubbell et al. |
| 5,865,814 A | 2/1999 | Tuch |
| 5,873,904 A | 2/1999 | Ragheb et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,891,192 A | 4/1999 | Murayama et al. |
| 5,897,955 A | 4/1999 | Drumheller |
| 5,914,182 A | 6/1999 | Drumheller |
| 5,916,870 A | 6/1999 | Lee et al. |
| 5,942,209 A | 8/1999 | Leavitt et al. |
| 5,948,428 A | 9/1999 | Lee et al. |
| 5,957,975 A | 9/1999 | Lafont et al. |
| 5,965,720 A | 10/1999 | Gryaznov et al. |
| 5,971,954 A | 10/1999 | Conway et al. |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,997,468 A | 12/1999 | Wolff et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,127,173 A | 10/2000 | Eckstein et al. |
| 6,129,761 A | 10/2000 | Hubbell |
| 6,153,252 A | 11/2000 | Hossainy et al. |
| 4,776,337 A | 12/2000 | Palmaz |
| 6,159,951 A | 12/2000 | Karpeisky et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,224,626 B1 | 5/2001 | Steinke |
| 6,228,845 B1 | 5/2001 | Donovan et al. |
| 6,245,103 B1 | 6/2001 | Stinson |
| 6,251,135 B1 | 6/2001 | Stinson et al. |
| 6,251,142 B1 | 6/2001 | Bernacca et al. |
| 4,733,665 C2 | 1/2002 | Palmaz |
| 6,379,379 B1 | 4/2002 | Wang |

FOREIGN PATENT DOCUMENTS

| | | |
|---|---|---|
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 970 711 | 1/2000 |
| GB | 2 247 696 | 3/1992 |
| JP | 2001-515934 | 9/2001 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 95/29647 | 11/1995 |
| WO | WO 99/34750 | 7/1999 |
| WO | WO 00/12147 | 3/2000 |
| WO | WO 00/44309 | 8/2000 |
| WO | WO 00/64506 | 11/2000 |
| WO | WO 00/74744 | 12/2000 |
| WO | WO 01/01890 | 1/2001 |
| WO | WO 01/67990 | 9/2001 |

OTHER PUBLICATIONS

Translation of a Notification of Refusal issued by JPO on Oct. 13, 2009, in connection with Appl. No. 2003-577971, 2 pgs.

Bull, *Parylene Coating for Medical Applications*, Medical Product Manufacturing News (1993).

Casper et al., *Fiber-Reinforced Absorbable Composite for Orthopedic Surgery*, Polymeric Materials Science and Engineering, 53:497-501 (1985).

Devanathan et al., *Polymeric Conformal Coating for Implantable Electronic Devices*, IEEE Transaction on Biomedical Engineering, vol. BME-27(11):671-675 (1980).

Hahn et al., *Biocompatibility of Glow-Discharge-Polymerized Films and Vacuum-Depositied Parylene*, J Applied Polymerc Sci, 38:55-64 (1984).

Hahn et al., *Glow Discharge Polymers as Coatings for Implanted Devices*, ISA, pp. 109-111 (1981).

Kelley et al., *Totally Resorbable High-Strength Composite Material*, Advances in Biomedical Polymers, 35:75-85 (1987).

Kubies et al., *Microdomain Structure In Polylactide-block-poly(ethylene oxide) Copolymer Films*, Biomaterials 21:529-536 (2000).

Muller et al., *Advances in Coronary Angioplasty: Endovascular Stents*, Coron Arter Dis, 1(4):438-448 (1998).

Nichols et al., *Electrical Insulation of Implantable Devices by Comosite Polymer Coatings*, ISA Transactions, 26(4):15-18 (1987).

Schatz, *A View of Vascular Stents*, Circulation, 79(2):445-457 (1989).

Schmidt et al., *Long-Term Implants of Parylene-C Coated Microelectrodes*, Med & Biol Eng & Comp, 26(1):96-101 (1988).

* cited by examiner

BIODEGRADABLE POLYMERS FOR USE WITH IMPLANTABLE MEDICAL DEVICES

RELATED APPLICATIONS

This application is a continuation-in-part of U.S. patent application Ser. No. 10/104,772, filed 20 Mar. 2002, now abandoned which is a continuation-in-part of application Ser. No. 09/548,533 filed on 13 Apr. 2000, now U.S. Pat. No. 6,527,801 B1, issued on 4 Mar. 2003.

FIELDS

This invention relates to the fields of organic chemistry, polymer science, material science and medical devices. In particular, it relates to biodegradable hydrophobic polymers of which stents can be fabricated or with which they can be coated.

BACKGROUND

In the treatment of vascular disease such as arteriosclerosis, intracoronary stent placement is a common adjunct to balloon angioplasty. Stents can eliminate vasospasm, attach dissections to a vessel wall, reduce negative remodeling, and maintain vessel patency. Stents, however, can also cause undesirable side effects. For example, the continued exposure of a stent to blood can lead to thrombus formation and the presence of a stent in a blood vessel can over time cause the blood vessel wall to weaken creating the potential for arterial rupture or formation of aneurisms. A stent can also become overgrown by tissue after its implantation such that its utility is diminished or eliminated while its continued presence may lead to a variety of complications such as the foregoing.

To ameliorate the above situation, stents can be fabricated from materials that are biodegradable and, if desired, bioabsorbable. The material selected must be not only biocompatible and biodegradable, it must have sufficient mechanical properties required of a stent. Such mechanical properties include, among others, sufficient strength to withstand the stresses to which the device will be subjected such as radial flexibility should the device be expandable as in the case of a balloon expandable stent and longitudinal flexibility to allow it to be advanced through a contorted vasculature and to adapt to a non-linear deployment site.

The above-described properties have been achieved at least in part using polymers such as polylactic acid, poly(lactic acid-co-glycolic acid) and polycaprolactone. These materials, however, typically biodegrade by bulk erosion which can result in large particles breaking away from the degrading stent. These particles, when released into the bloodstream, may cause emboli and/or other complications.

What is needed are biocompatible, biodegradable polymers that have the mechanical properties required of a stent and that biodegrade by surface rather than bulk erosion. Such polymers should also be useful to coat implantable medical devices for use as drug delivery systems since the lack of a bulk erosion propensity should drastically reduce if not eliminate flaking off of large particles of the coating when implanted in a patient. The current invention provides compositions comprising such polymers.

SUMMARY

Thus, one aspect of this relates to a stent fabricated from or coated with a composition comprising a bioerodible hydrophobic polymer having a plurality of water-labile bonds wherein the polymer has sufficient mechanical strength to withstand forces present in mammalian vascular systems and also bioerodes from its surface inward.

In an aspect of this invention the water-labile bonds comprise one or more bond type(s) independently selected from the group consisting of ester bonds, orthoester bonds, anhydride bonds, imide bonds and combinations thereof.

In an aspect of this invention the water labile bonds comprise a constitutional unit derived from trimellitylimido-L-tyrosine.

In an aspect of this invention the constitutional unit derived from trimellitylimido-L-tyrosine comprises from about 20 to about 40 wt % of the hydrophobic polymer.

In an aspect of this invention the water labile bonds comprise one or more constitutional unit(s) derived from a compound or compounds independently selected from the group consisting of sebacic acid, di-ortho-carboxyphenyl sebacate, salicylic acid, maleic acid, 1,3-bis-para-carboxyphenoxypropane, 1,6-bis-para-carboxyphenoxy hexane, trimellitylimido-L-tyrosine, terephthalic acid, L-lactic acid, D-lactic acid, DL-lactic acid, L-aspartic acid and 4-hydroxy-L-proline.

In an aspect of this invention the water-labile bonds further comprise one or more constitutional unit(s) derived from a compound or compounds selected from the group consisting of 1,10-decanediol, ethylene glycol, and 1,2,6-hexanetriol.

In an aspect of this invention the water-labile bond(s) comprise one or more constitutional unit(s) derived from a compound or compounds selected from the group consisting of tri(1C-12C)alkyl ortho(1C-12C)carboxylates.

In an aspect of this invention the water-labile bond(s) further comprise one or more constitutional unit(s) derived from a compound or compounds selected from the group consisting of tri(1C-12C)alkyl ortho(1C-12C)carboxylates.

In an aspect of this invention the hydrophobic polymer comprises constitutional units derived from trimellitylimido-L-tyrosine, sebacic acid and 1,3-bis(para-carboxyphenoxy)propane.

In an aspect of this invention the hydrophobic polymer comprises constitutional units derived from 1,6-bis(para-carboxyphenoxy)hexane and di-ortho-carboxyphenoxy-sebacate acetic anhydride.

In an aspect of this invention the hydrophobic polymer comprises constitutional units derived from maleic acid and sebacic acid.

In an aspect of this invention the hydrophobic polymer comprises constitutional units derived from 1,3-bis(para-carboxyphenoxy)propane, sebacic acid and salicylic acid.

In an aspect of this invention the hydrophobic polymer comprises constitutional units derived from 1,2,6-hexanetriol and trimethylorthoacetate.

In an aspect of this invention the hydrophobic polymer comprises constitutional units derived from poly(ethylene glycol) and poly(butylene terephthalate).

In an aspect of this invention, the stent further comprises one or more therapeutic substance(s).

In an aspect of this invention the therapeutic substance(s) is(are) selected from the group consisting of actinomycin D, paclitaxel, docetaxel, methotrexate, azathioprine, vincristine, vinblastine, fluorouracil, doxorubicin hydrochloride, mitomycin, sodium heparin, low molecular weight heparins, heparinoids, heparin derivatives having hydrophobic counter ions, hirudin, argatroban, forskolin, vapiprost, prostacyclin, dextran, D-phe-pro-arg-chloromethylketone, dipyridamole, glycoprotein IIb/IIIa platelet membrane receptor antagonist antibody, recombinant hirudin, and thrombin, angiopeptin, captopril, cilazapril, lisinopril, nifedipine, colchicine, fibroblast growth factor (FGF) antagonists, fish oil (ω-3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide, permirolast potassium, alpha-interferon, genetically engineered epithelial cells, rapamycin, everolimus and dexamethasone.

In an aspect of this invention the biodegradable hydrophobic polymer further comprises one or more constitutional unit(s) derived from one or more therapeutic substance(s).

In an aspect of this invention the therapeutic substance(s) which comprise one or more constitutional units is(are) selected from the group consisting of salicylic acid, nitric oxide, poly(ethylene glycol), heparin, low molecular weight heparin, hepariniods and hyaluronic acid.

In an aspect of this invention the biodegradable hydrophobic polymer comprises a block copolymer of polyethylene glycol and poly(butylene terephthalate).

In an aspect of this invention the stent further comprises an alternative polymer.

DETAILED DESCRIPTION

The polymers describe herein are useful for the fabrication and/or coating of implantable medical devices, in particular stents, in that they not only have the requisite mechanical properties but they also biodegrade by surface erosion rather than by bulk erosion. They thus would be expected to at least drastically reduce and preferably eliminate large particle formation and release during biodegradation.

Definitions

As used herein, "alkyl" refers to a straight or branched chain fully saturated (no double or triple bonds) hydrocarbon group. An alkyl group of this invention may comprise from 1 to 20 carbon atoms, more preferably at present 1 to 12 carbon atoms and still more preferably at present 1 to 6 carbon atoms.

decomposition of a device or coating that is comprised of the polymer(s). The process may be catalyzed by enzymes and other endogenous biological compounds.

As used herein, "hydrophobic" refers to a polymer that lacks an affinity for water. That is, it tends to repel water, to not dissolve in, mix with or be wetted by water or to do so only to a very limited degree and to not absorb water or, again, to do so only to a very limited degree. With regard to polymers, generally hydrophobicity increase with increasing alkyl content in the polymer backbone, that is, the greater the alkyl content in one or more of the constitutional units of the polymer. The hydrophobicity of a polymer may be characterized by determining the static contact angle of droplets of distilled water on a surface of the polymer. The greater the contact angle, the more hydrophobic the polymer. Generally speaking, a contact angle of greater than 90° indicates a hydrophobic polymer. The specifics or such measurements will not be presented here since they are well-known to those skilled in the art.

As used herein, "water-labile bonds" refers to the bonds in chemical functional groups that hydrolyze; that is, break apart to give two separate molecules, by reaction with water, a reaction that may be affected by the catalytic influence of, without limitation, an acid, base, nucleophile or enzyme. Examples of water-labile bonds include, without limitation, the C—O bond of an ester, orthoester or anhydride and the C—N bond of an amide or imide.

As used herein, the term "constitutional unit" refers to the monomer-derived chemical units of a polymer. For example, in the polymer

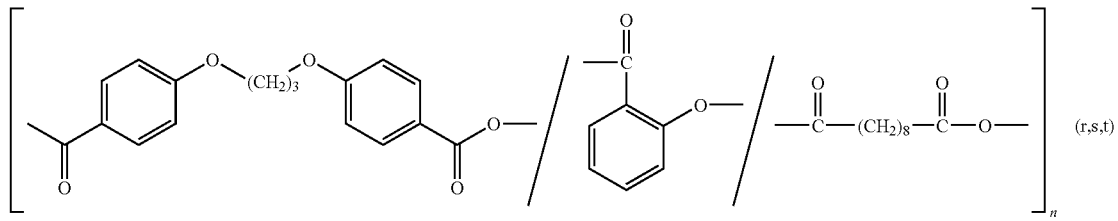

As used herein, "trialkyl orthoalkylcarboxylate" refers to a compound having the chemical structure:

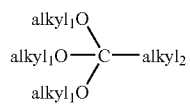

with alkyl as defined above. Alkyl$_1$ and alkyl$_2$ may be the same or different.

As used herein, "fabrication" or "fabricating" refers to the construction of, or formation of a device from a composition comprising a polymer of this invention. The fabrication, that is, the construction or formation, may include other materials but the primary material(s) is(are) the polymer(s) described herein that provide the device with the characteristics likewise discussed herein.

As used herein, "biodegradable" and "bierodible" unless otherwise expressly stated are interchangeable and refer to the cleaving of bonds in a polymer chain primarily by aqueous hydrolysis as the result of contact with water in blood and other bodily fluids at physiological pH, i.e., around 7-7.5, resulting in the fragmentation of the polymer and eventual the chemical groups shown comprise the constitutional units whereas the actual monomers from which they are derived may be substantially different. For example, without limitation, the monomer from which the

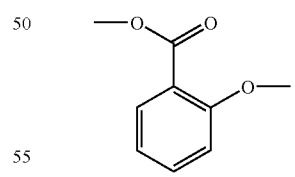

constitutional unit is derived might be

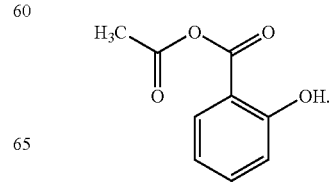

In general, a wide variety of monomers may afford the same constitutional unit depending on the polymerization method employed. With regard to the polymers herein, any monomer that results in the formation of the constitutional units shown herein is within the scope of this invention.

As used herein, a therapeutic substance or agent refers to a compound that, when administered to a patient has a beneficial effect relating to the health and well-being of the patient. Therapeutic substances may be, without limitation, small molecule drugs, large molecule drugs, peptides, antibodies, proteins, enzymes, oligonucleotides, DNAs or RNAs.

As used herein, the "vascular system" refers to the arteries and veins that carry blood throughout the body. This includes, without limitation, the cardiovascular system, those arteries and veins that carry blood directly to the heart and the peripheral vascular system, those arteries and veins that carry blood to the peripheral organs such as, without limitation, the arms, legs, kidneys and liver.

As used herein, a "composition" refers to a physical mixture of discrete components brought together to accomplish a particular objective. For example, a stent or a coating for a stent may comprise a composition comprising, without limitation, one or more polymers, one or more therapeutic substances and one or more additives such as plasticizers and the like.

Discussion

Bulk erosion occurs when hydrolytic forces gain access to water-labile bonds throughout the mass of a polymer at a rate that competes effectively with the rate of hydrolysis of the water-labile bonds. The result is uncontrollable degradation throughout the entire mass of the polymer that can result in the release of large pieces of polymer that can cause thrombi and other problems at sites potentially distant from the original location of the polymer. Water accessibility to the labile bonds is governed largely by the hydrophobicity of the polymer, which in turn depends on the hydrophobicity of the individual monomers and the relative amount of each monomer in the polymer. In addition, the level of reactivity of the water-labile bonds in the polymer will also affect how a polymer degrades. If the bonds are sufficiently labile, i.e., if they hydrolyze at a sufficiently rapid rate, then bonds exposed at the surface of a mass of polymer will naturally hydrolyze sooner than those to which water must first gain access through the bulk of the polymer. Thus a suitable balance of hydrophobicity and bond lability should insure that a biodegradable hydrophobic polymer will erode from an exposed surface of the polymer inward rather than in bulk mode as described above.

The biodegradable hydrophobic polymers herein contain water-labile bonds interconnecting the constitutional units of the polymer. The water-labile bonds include, without limitation, esters, orthoesters, anhydrides and imides. Other bonds such as, without limitation, ethers, amides, urethanes, etc. may also be present in the polymer but the propensity of the polymer to surface erosion rather than bulk erosion relates to the overall hydrophobicity of the polymer and the content and reactivity of the water-labile linkages in the polymer. That is, the overall hydrophobic nature of the polymer precludes or at least inhibits the incursion of water into the polymer's interior while water-labile linkages exposed on the polymer's surface hydrolyze resulting in the degradation of the polymer from the outermost surface of the bulk polymer, be it a device made of the polymer of a coating of the polymer on a device, inward rather than by bulk mode erosion.

When the implantable medical device is a stent, imide and/or ester bonds are presently preferred to confer on the polymer the necessary strength to provide the support that is required of such device. If the polymer is to be used as a coating on an implantable device, imide and/or ester bonds impart sufficient strength to the layer of polymer to prevent the coating from flaking off or otherwise becoming detached as the coated device undergoes distortion caused by radial and longitudinal fluctuations as it is transported to its site of implantation and as it is deployed once at the site.

The number of imide or ester bonds that are incorporated in the polymer material not only affects the ultimate strength and flexibility of the stent and/or the stent coating, but also affects the rate at which the material degrades when subjected to blood flow.

A polymer useful for the fabrication and/or coating of an implantable medical device, in particular at present a stent, is a terpolymer (three constitutional units) comprised of trimellitylimido-L-tyrosine (TMIT):

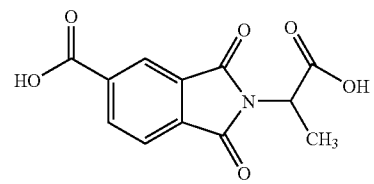

sebacic acid (SBA), HOOC—(CH$_2$)$_8$—COOH, and 1,3-bis (para-carboxyphenoxy)-propane (PCPP):

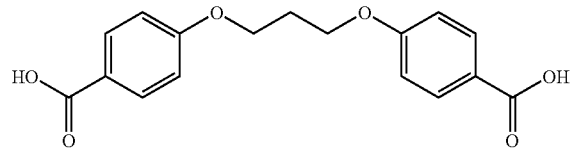

The general formula of this polymer, poly(TMIT-co-SBA-co-PCPP), is:

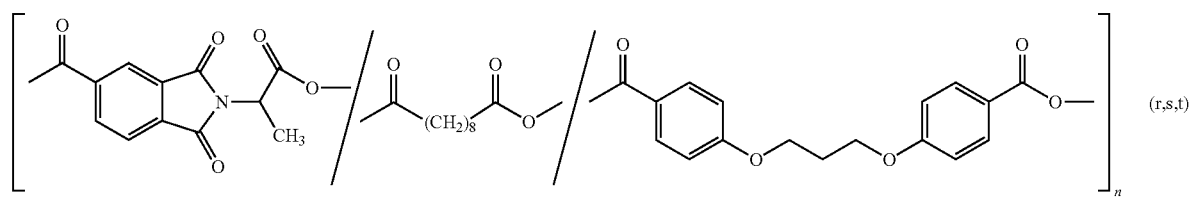

As used herein, the formula [-x-/-y-/-z-/ . . . ] (r, s, t, . . . ), represents a polymer in which x, y, z, etc. are the constitutional units of the polymer. The formula as written, unless expressly stated to be otherwise, refers to any of a regular alternating polymer, a random alternating polymer, a regular block polymer, a random block polymer or a purely random polymer. A regular alternating polymer has the general structure, x-y-z-x-y-z-x-y-z- . . . . A random alternating polymer has the general structure, x-y-x-z-x-y-z-y-z-x-y- . . . , it being understood that the exact juxtaposition of the various constitution units may vary. A regular block polymer, with the same proviso regarding juxtaposition of constitutional units apply equally to the juxtaposition of blocks, to the number of constitutional units in each block and to the number of blocks, has the general structure, x-x-x-y-y-y-z-z-z-x-x-x . . . , while a random block polymer has the general structure, x-x-x-z-z-x-x-y-y-y-z-z-x-x-z-z-z- . . . .

In the above general polymeric structure, r, s, t, etc., refer to the weight percent (wt %) of each constitutional unit and n refers to the average molecular weight of the polymer. The average molecular weight of a polymer herein may be determined by a number of methods known to those skilled in the art but, at present, size exclusion chromatography is the preferred method. For poly(TMIT-SBA-PCPP) to have sufficient strength as a stent, a content of the imide-containing constitutional unit is presently preferably between about 20% and about 40 wt %.

Another polymer useful for the fabrication and/or coating of an implantable medical device is the copolymer of 1,6-bis(para-carboxyphenoxy)hexane (PCPX):

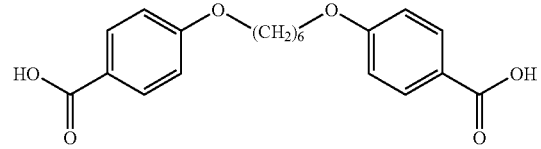

and di-ortho-carboxyphenyl sebacate anhydride:

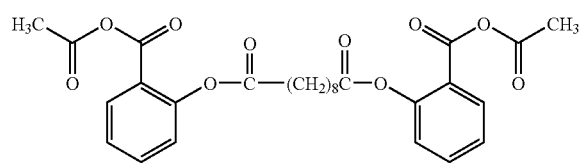

A general formula of the above copolymer made of the above monomers, that is, poly(PCPX-co-OCPSA) is:

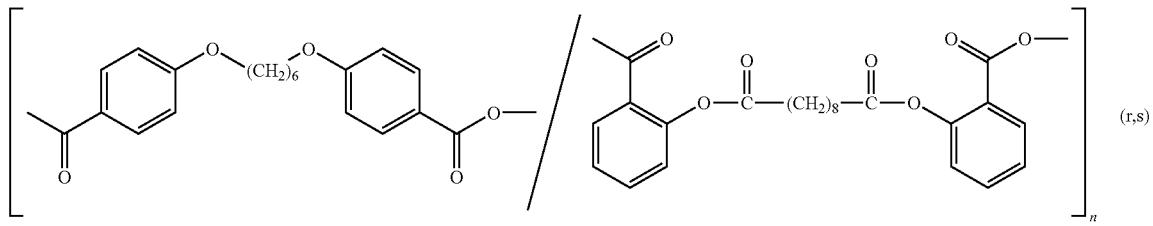

As above, r and s refer to the wt % of the two constitutional units of the polymer and n refers to the average molecular weight of the polymer.

It should be noted that one of the degradation products of poly(PCPX-co-OCPSA) is salicylic acid (SA), which is an antiplatelet agent in its own right and which may provide additional beneficial effects upon degradation at the site of implantation.

Still another polymer useful for the fabrication and/or coating of an implantable medical device is the polyanhydride obtained from the copolymerization of maleic acid (MA), HOOC—CH=CH—COOH, or a suitable derivative thereof and sebacic acid (SBA), HO(O)C(CH$_2$)$_8$C(O)OH, or a suitable derivative thereof:

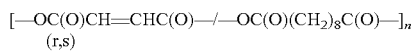

in which, as before, r and s refer to the wt % of each constitutional unit and n is the average molecular weight of the polymer.

Still another polymer useful for the fabrication and/or coating of an implantable medical device of this invention is the terpolymer obtained from the polymerization of PCPP, SBA and SA:

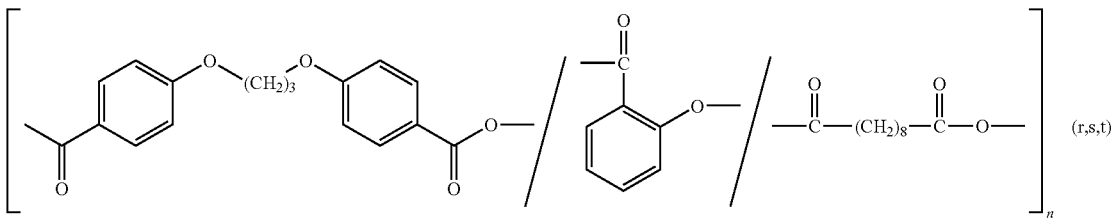

Again, r, s, and t represent the wt % of each constitutional unit and n is the average molecular weight of the polymer.

Yet another polymer useful for the fabrication and/or coating of an implantable medical device is that obtained by the polymerization of lactic acid (unless expressly stated to be otherwise, "lactic acid" refers herein to any one of L-lactic acid, D-lactic acid or DL-lactic acid) with multifunctional diacids such as aspartic acid, $HOOCCH_2CH(NH_2)COOH$:

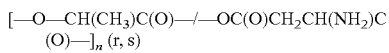

wherein r and s represent the wt % percent of each constitutional unit and n represents the average molecular weight of the polymer.

While polyesters are generally susceptible to bulk erosion, a suitable balance between overall hydrophobicity of the polymer and the water-lability of its ester groups will provide a polymer useful for the fabrication and/or coating of an implantable medical device. Such a polyester is the product of polymerization of 1,10-decanediol with lactic acid:

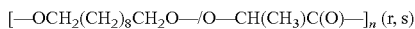

wherein r and s represent the wt % of each constitutional unit and n is the average molecular weight of the polymer. To achieve the proper balance between hydrophobicity and water-lability, it is present preferred that s be less than about 30 wt %.

Another polyester that can be used to fabricate and/or coat implantable medical devices is a block-copolymer of lactic acid with ethylene glycol (EG). Such block copolymers can be prepared by polymerization of lactic acid and ethylene glycol induced by a poly(ethylene glycol) (PEG) macroinitiator.

The above block copolymer will degrade in the presence of water in the body to give lactic acid and PEG. Lactic acid is relatively innocuous biologically while PEG is known to reduce smooth muscle cell proliferation and thus should aid in the inhibition of restenosis when the implantable medical device is a vascular stent.

A further PEG-containing polyester suitable for fabrication or coating of an implantable medical device in accordance with the present invention is a block-copolymer of PEG with polybutyleneterephthalate (PBT). This block-copolymer can be obtained by trans-esterification of the butyl ester end groups of PBT with PEG.

An example of a polyorthoester suitable making a stent and/or a stent coating in accordance with the present invention includes the product of transesterification of trimethylorthoacetate with 1,2,6-hexanetriol.

For any of the polyester-containing polymers described above, a content of ester-derived units of between about 20 wt % and about 40 wt % is presently preferred in order to obtain a medical device having sufficient strength for use as a stent.

With regard to each of the polymers exemplified herein, the value of n is presently preferably greater than 50,000 Da. The upper end of the molecular weights of the polymers herein is limited only by the limits of processability of the polymer. That is, above a certain n, the bulk properties of the polymer are such that the polymer is not processable, i.e., cannot be melted, molded, extruded, coated, etc. under commercially viable conditions. With regard to any particular polymer, that value of n will be readily apparent to those skilled in the art. Likewise, the values of r, s and t, except where presently preferred ranges are expressly set forth herein, will be readily determinable by those skilled in the art without undue experimentation based on the disclosures herein.

Table 1 presents the summary of the above polymers and also shows the monomers used to synthesize them.

TABLE 1

Biodegradable hydrophobic polymers useful for the fabrication or coating of implantable medical devices

| No. | Polymer and abbreviation | Monomer 1 and abbreviation | Monomer 2 and abbreviation | Monomer 3 and abbreviation |
|---|---|---|---|---|
| 1 | Poly[trimellitylimido-L-tyrosine-co-sebacic acid-co-1,3-bis(para-carboxyphenoxy)propane], p(TMIT-SBA-PCPP) | Trimellitylimido-L-tyrosine (TMIT) | Sebacic acid (SBA) | 1,3-bis (para-carboxyphenoxy) propane (PCPP) |
| 2 | Poly[1,6-bis(para-carboxyphenoxy)hexane-co-ortho-carboxyphenoxy sebacate anhydride], p(PCPX-OCPSA) | 1,6-bis (para-carboxyphenoxy) hexane (PCPX) | di-ortho-carboxyphenoxy sebacate anhydride (OCPSA) | None |
| 3 | Poly[1,3-bis(para-carboxyphenoxy) propane-co salicylic acid-co-sebacic acid], p(PCPP-SBA-S | 1,3-bis(para-carboxyphenoxy) propane (PCPP) | Sebacic acid or anhydride (SBA) | Salicylic acid (SA) |
| 4 | Poly(maleic acid-co-sebacic acid), p(MA-SBA) | Maleic acid (MA) | Sebacic acid or anhydride (SBA) | None |
| 5 | Poly(L-lactic acid-co-L-aspartic acid), p(LLA-LAspA) | L-lactic acid (LLA) | L-aspartic acid (LAspA) | None |

TABLE 1-continued

Biodegradable hydrophobic polymers useful for the fabrication or coating of implantable medical devices

| No. | Polymer and abbreviation | Monomer 1 and abbreviation | Monomer 2 and abbreviation | Monomer 3 and abbreviation |
|---|---|---|---|---|
| 6 | Poly(DL-lactic acid-co-L-aspartic acid), p(DLLA-LAspA) | DL-lactic acid (DLLA) | L-aspartic acid (LAspA) | None |
| 7 | Poly(L-lactic acid), pLLA | L-lactic acid (LLA) | None | None |
| 8 | Poly(DL-lactic acid), pDLLA | DL-lactic acid (DLLA) | None | None |
| 9 | Poly(L-lactic acid-co-ethylene glycol), p(LLA-EG) | L-lactic acid (LLA) | Ethylene glycol (EG) | None |
| 10 | Poly(DL-lactic acid-co-ethylene glycol), p(DLLA-EG) | DL-lactic acid (DLLA) | Ethylene glycol (EG) | None |
| 11 | Poly(ethylene glycol-co-butylene terephthalate), p(EG-BT) | Ethylene glycol (EG) | Butylene terephthalate) (BT) | None |
| 12 | Poly(4-hydroxy-L-proline ester), p(HOXPE) | 4-hydroxy-L-proline (HOXP) | None | None |
| 13 | Poly(1,10-decanediol-co-L-lactic acid), p(DCD-LLA) | 1,10-decanediol (DCD) | L-lactic acid (LLA) | None |
| 14 | Poly(1,10-decanodiol-co-D,L-lactic acid), p(DCD-DLLA) | 1,10-decanediol (DCD) | DL-lactic acid (DLLA) | None |
| 15 | Poly(1,2,6-hexanetriol-co-trimethylorthoacetate), p(HTOL-TMAC) | 1,2,6-hexanetriol (HTOL) | Trimethylorthoacetate (TMAC) | None |
| 16 | Poly(hydroxybutyrate) (PHB) | Hydroxybutyrate (HB) | None | None |
| 17 | Poly(hydroxyvalerate) (PHV) | Hydroxyvalerate (HV) | None | None |
| 18 | Poly(hydroxy-butyrate-valerate) (PHBV) | Hydroxybutyrate (HB) | Hydroxyvalerate (HV) | N/A |

Increasing the imide content, i.e., the wt % of imide, of a polymer herein results in higher material strength. In addition, flexibility of polyanhydrides like p(MA-SBA) can be increased by increasing the wt % of maleic acid dimer.

One or more therapeutic agent(s) may be optionally added to the polymers to create a composition useful for localized sustained delivery of the agents to a patient at the site of implantation of a medical device. The therapeutic agent may be incorporated during the polymerization process or it may be blended with the polymer after it is formed. Blending may be accomplished either in solution or in a melt state. Some therapeutic agents can be chemically incorporated into the backbone of a polymer herein, or can be chemically bonded to the polymer backbone as a pendant group. Therapeutic agents that could be incorporated into the backbone of, or as a pendent group to, a polymer herein include, without limitation, salicylic acid, nitric oxide, PEG, heparin, low molecular weight heparins, heparinoids and hyaluronic acid.

Examples, without limitation, of therapeutic agents that may be used with the polymers of this invention include, without limitation, antiproliferative substances such as actinomycin D, or derivatives and analogs thereof. Synonyms of actinomycin D include dactinomycin, actinomycin IV, actinomycin $I_1$ actinomycin $X_1$, and actinomycin $C_1$. The Therapeutic agent may be an antineoplastic, anti-inflammatory, antiplatelet, anticoagulant, antifibrin, antithrombin, antimitotic, antibiotic, antiallergic or antioxidant substances. Examples of antineoplastics and/or antimitotics include paclitaxel, docetaxel, methotrexate, azathioprine, vincristine, vinblastine, fluorouracil, doxorubicin hydrochloride, and mitomycin. Examples of antiplatelets, anticoagulants, antifibrin, and antithrombins include sodium heparin, low molecular weight heparins, heparinoids, heparin derivatives having hydrophobic counter ions, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and its derivatives (one example of which is everolimus available from Novartis Corp.), and dexamethasone.

As used herein, "low molecular weight heparins" refers to fragments of unfractionated heparin. Whereas unfractionated heparin is a heterogeneous mixture of highly sulfated polysaccharide chains ranging in molecular weight from about 3,000 to about 30,000 DA, low molecular weight heparins have a molecular weight between about 4,000 and about 6,000 DA. The term "low molecular weight heparins" and the molecules to which the term refers are well-known to those skilled in the medical arts.

As used herein, "heparinoids" refers to naturally-occurring and synthetic highly sulfated polysaccharides that are structurally similar to heparin. Examples, without limitation, of heparinoids are danaparoid sodium, fondaparinux and idraparinux. As with low molecular weight heparins, heparinoids are well-known to those skilled in the medical arts.

Examples of the implantable medical device include stents, stent-grafts, grafts (e.g., aortic grafts), artificial heart valves, cerebrospinal fluid shunts, pacemaker electrodes, coronary shunts and endocardial leads (e.g., FINELINE and ENDOTAK, available from Guidant Corporation). The underlying structure of the device can be of virtually any design. A presently preferred implantable medical device is a vascular stent.

A vascular stent may be formed by any of a number of well-known methods including the extrusion of the polymer into the shape of a tube. Pre-selected patterns of voids can then be formed into the tube in order to define a plurality of spines or struts that impart a degree of flexibility and expandability to the tube. Alternatively, the drug loaded polymer may be applied to the selected surfaces of a stent made of, for example, stainless steel. The stent can be, for example, immersed in the molten polymer or sprayed with a liquid form of the polymer. Or a polymer may be extruded in the form of a tube which is then co-drawn with a tube of stainless steel, or other suitable metallic materials or alloys. By co-drawing two tubes of the polymer with the metal tube, one positioned about the exterior of the metal tube and another positioned within the metal tube, a tube having multi-layered walls is formed. Subsequent perforation of the tube walls to define a pre-selected pattern of spines or struts imparts the desired flexibility and expandability to the tube to create a stent.

The polymer listed in Table 1 can be blended or coated with one or more additional polymers, referred to herein as "alternative polymers." One example of an alternative polymer is poly(ethylene-co-vinyl alcohol), also known under the trade name EVAL and distributed commercially by Aldrich Chemical Company of Milwaukee, Wis. EVAL is also manufactured by EVAL Company of America, Lisle, Ill. EVAL is a product of hydrolysis of ethylene-vinyl acetate copolymers. EVAL may also be a terpolymer and may include up to 5% (molar) of units derived from styrene, propylene and other suitable unsaturated monomers.

Other examples of alternative polymers include poly(hydroxyvalerate), polycaprolactone, poly(lactide-co-glycolide), poly(hydroxybutyrate), poly(hydroxybutyrate-co-valerate), polydioxanone, poly(glycolic acid), polyphosphoester, polyphosphoester urethane, poly(amino acids), cyanoacrylates, poly(iminocarbonate), copoly(ether-esters) (e.g. PEO/PLA), polyalkylene oxalates, polyphosphazenes, polyurethanes, silicones, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene fluoride and polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, and biomolecules, such as fibrin, fibrinogen, cellulose, starch, collagen and hyaluronic acid.

EXAMPLES

The following examples are provided for illustrative purposes only and are not intended nor should they be construed as limiting the scope of this invention in any manner whatsoever.

Example 1

A first composition can be prepared by mixing the following components:

(a) between about 0.1 mass % and about 15 mass %, for example, about 1.0 mass % of poly(LLA-EG);

(b) between about 0.1 mass % and about 10.0 mass %, for example, about 2.0 mass % of poly(DLLA);

(c) between about 0.05 mass % and about 2.0 mass %, for example, about 1.0 mass % of a biologically active substance such as rapamycin, or a derivative or analog thereof; and (d) the balance, dioxane solvent.

The first composition is applied onto the stent and dried to form a drug-polymer layer. The composition is applied onto the stent by any conventional method, for example, by spraying or dipping. A primer layer (e.g., the above formulation without the therapeutically active substance) can be optionally applied on the surface of the bare stent prior to the application of the drug-polymer layer.

For a stent having a length of 13 mm and diameter of 3 mm, the total amount of solids of the matrix layer can be about 300 micrograms (corresponding to the thickness of between about 15 and 20 microns). "Solids" means the amount of the dry residue deposited on the stent after all volatile organic compounds (e.g., the solvent) have been removed.

A second composition can be prepared by mixing the following components:

(a) between about 0.1 mass % and about 15 mass %, for example, about 1.0 mass % of poly(LLA-EG);

(b) between about 0.1 mass % and about 10.0 mass %, for example, about 2.0 mass % of poly(DLLA); and (c) the balance, dioxane solvent.

The second composition is applied onto the dried drug-polymer layer and dried, to form an optional topcoat layer. The topcoat layer can be applied by any conventional method and can have, for example, a total solids weight of about 200 µg.

A third composition can be prepared by mixing the following components:

(a) between about 0.1 mass % and about 15 mass %, for example, about 1.125 mass % of poly(LLA-EG);

(b) between about 0.1 mass % and about 10.0 mass %, for example, about 0.75 mass % of poly(DLLA); and (c) the balance, dioxane solvent.

The third composition is applied onto the topcoat layer and dried, to form an optional finishing coat layer. The finishing coat layer can be applied by any conventional method and can have, for example, a total solids weight of about 150 µg.

Example 2

A first composition can be prepared by mixing the following components:

(a) between about 0.1 mass % and about 15 mass %, for example, about 1.0 mass % of poly(LLA-EG);

(b) between about 0.1 mass % and about 10.0 mass %, for example, about 2.0 mass % of poly(DLLA);

(c) between about 0.05 mass % and about 2.0 mass %, for example, about 1.0 mass % of estradiol; and (d) the balance, dioxane solvent.

The first composition is applied onto a stent to form a drug-polymer layer with about 300 µg of total solids.

A second composition can be prepared by mixing the following components:

(a) between about 0.1 mass % and about 15 mass %, for example, about 1.0 mass % of poly(LLA-EG);

(b) between about 0.1 mass % and about 10.0 mass %, for example, about 2.0 mass % of poly(DLLA); and (c) the balance, dioxane solvent.

The second composition is applied onto the dried drug-polymer layer and dried to form an optional topcoat layer. The topcoat layer can have, for example, a total solids weight of about 200 µg.

A third composition can be prepared by mixing the following components:

(a) between about 0.1 mass % and about 15 mass %, for example, about 1.125 mass % of poly(LLA-EG);

(b) between about 0.1 mass % and about 10.0 mass %, for example, about 0.75 mass % of poly(DLLA); and (c) the balance, dioxane solvent.

The third composition is applied onto the topcoat layer and dried, to form the optional finishing coat layer. The finishing coat layer can have, for example, a total solids weight of about 150 μg.

Example 3

A first composition can be prepared by mixing the following components:
(a) between about 0.1 mass % and about 15 mass %, for example, about 2.0 mass % of poly(PCPP-SA-SBA);
(b) between about 0.05 mass % and about 2.0 mass %, for example, about 1.0 mass % of estradiol; and
(c) the balance, a solvent mixture containing about equal mass amounts of dimethylacetamide (DMAC) and tethrahydrofurane (THF).

The first composition is applied onto a stent to form a drug-polymer layer with about 300 μg of total solids.

A second composition can be prepared by mixing the following components:
(a) between about 0.1 mass % and about 15 mass %, for example, about 2.0 mass % of poly(PCPP-SA-SBA); and
(b) the balance, a solvent mixture containing about equal mass amounts of DMAC and THF.

The second composition is applied onto the dried drug-polymer layer to form an optional topcoat layer. The topcoat layer can have, for example, a total solids weight of about 200 μg.

The three examples of the formulations above can be summarized as shown in Table 2.

While certain embodiments of the present invention are described above, it is understood that changes and modifications will become apparent to those skilled in the art based on the disclosures herein; all such changes and disclosures are within the scope of this invention.

TABLE 2

A Summary of the Formulations of Examples 1-3

| Example | Polymer in matrix layer | Drug in matrix layer | Solids in dry matrix layer, μg | Polymer in topcoat layer | Solids in the dry topcoat layer, μg | Polymer in finishing layer | Solids in the dry finishing layer, μg |
|---|---|---|---|---|---|---|---|
| 1 | p(LLA-EG), 1% and p(DLLA), 2% | a derivative of rapamycin, 1.0% | 300 | p(LLA-EG), 1% and p(DLLA), 2% | 200 | p(LLA-EG), 1.125% and p(DLLA), 0.75% | 150 |
| 2 | p(LLA-EG), 1% and p(DLLA), 2% | estradiol, 1.0% | 300 | p(LLA-EG), 1% and p(DLLA), 2% | 200 | p(LLA-EG), 1.125% and p(DLLA), 0.75% | 150 |
| 3 | p(PCPP-SA-SBA), 2% | estradiol, 1.0% | 300 | p(PCPP-SA-SBA), 2% | 200 | None | N/A |

What is claimed:

1. A stent fabricated from or coated with a composition comprising a bioerodible hydrophobic polymer having a plurality of water-labile bonds wherein the polymer has sufficient mechanical strength to withstand forces present in mammalian vascular systems and also bioerodes from its surface inward.

2. The stent of claim 1, wherein the water-labile bonds comprise one or more bond type(s) independently selected from the group consisting of ester bonds, orthoester bonds, anhydride bonds, imide bonds and combinations thereof.

3. The stent of claim 2, wherein the water labile bonds comprise a constitutional unit derived from trimellitylimido-L-tyrosine.

4. The stent of claim 3, wherein the constitutional unit derived from trimellitylimido-L-tyrosine comprises from about 20 to about 40 wt % of the hydrophobic polymer.

5. The stent of claim 2, wherein the water labile bonds comprise one or more constitutional unit(s) derived from a compound or compounds independently selected from the group consisting of sebacic acid, di-ortho-carboxyphenyl sebacate, salicylic acid, maleic acid, 1,3-bis-para-carboxyphenoxypropane, 1,6-bis-para-carboxyphenoxy-hexane, trimellitylimido-L-tyrosine, terephthalic acid, L-lactic acid, D-lactic acid, DL-lactic acid, L-aspartic acid and 4-hydroxy-L-proline.

6. The stent of claim 5, wherein the water-labile bonds further comprise one or more constitutional unit(s) derived from a compound or compounds selected from the group consisting of 1,10-decanediol, ethylene glycol, and 1,2,6-hexanetriol.

7. The stent of claim 6, wherein the water-labile bond(s) further comprise one or more constitutional unit(s) derived from a compound or compounds selected from the group consisting of tri(1C-12C)alkyl ortho(1C-12C)carboxylates.

8. The stent of claim 2, wherein the water-labile bond(s) comprise one or more constitutional unit(s) derived from a compound or compounds selected from the group consisting of tri(1 C-12C)alkyl ortho(1 C-12C)carboxylates.

9. The stent of claim 1, wherein the hydrophobic polymer comprises constitutional units derived from trimellitylimido-L-tyrosine, sebacic acid and 1,3-bis(para-carboxyphenoxy) propane.

10. The stent of claim 1, wherein the hydrophobic polymer comprises constitutional units derived from 1,6-bis(para-carboxyphenoxy)hexane and di-ortho-carboxyphenoxysebacate acetic anhydride.

11. The stent of claim 1, wherein the hydrophobic polymer comprises constitutional units derived from maleic acid and sebacic acid.

12. The stent of claim 1, wherein the hydrophobic polymer comprises constitutional units derived from 1,3-bis(para-carboxyphenoxy)propane, sebacic acid and salicylic acid.

13. The stent of claim 1, wherein the hydrophobic polymer comprises constitutional units derived from 1,2,6-hexanetriol and trimethylorthoacetate.

14. The stent of claim 1, wherein the hydrophobic polymer comprises constitutional units derived from poly(ethylene glycol) and poly(butylene terephthalate).

15. The stent of claim 1, further comprising one or more therapeutic substance(s).

16. The stent of claim 15, wherein the therapeutic substance(s) is(are) selected from the group consisting of actinomycin D, paclitaxel, docetaxel, methotrexate, azathioprine, vincristine, vinblastine, fluorouracil, doxorubicin hydrochloride, mitomycin, sodium heparin, low molecular weight heparins, heparinoids, heparin derivatives having hydrophobic counter ions, hirudin, argatroban, forskolin, vapiprost, prostacyclin, dextran, D-phe-pro-arg-chloromethylketone, dipyridamole, glycoprotein IIb/IIIa platelet membrane receptor antagonist antibody, recombinant hirudin, and thrombin, angiopeptin, captopril, cilazapril, lisinopril, nifedipine, colchicine, fibroblast growth factor (FGF) antagonists, fish oil (ω-3- fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide, permirolast potassium, alpha-interferon, genetically engineered epithelial cells, rapamycin, everolimus and dexamethasone.

17. The stent of claim 1, wherein the biodegradable hydrophobic polymer further comprises one or more constitutional unit(s) derived from one or more therapeutic substance(s).

18. The stent of claim 17, wherein the therapeutic substance(s) is(are) selected from the group consisting of salicylic acid, nitric oxide, poly(ethylene glycol), heparin, low molecular weight heparin, hepariniods and hyaluronic acid.

19. The stent of claim 1, wherein the biodegradable hydrophobic polymer comprises a block copolymer of polyethylene glycol and poly(butylene terephthalate).

20. The stent of claim 1, further comprising an alternative polymer.

* * * * *